US007138519B2

(12) United States Patent
Morgan

(10) Patent No.: US 7,138,519 B2

(45) Date of Patent: Nov. 21, 2006

(54) PROCESS FOR EXTRACTION OF β-GLUCAN FROM CEREALS AND PRODUCTS OBTAINED THEREFROM

(75) Inventor: Keith Raymond Morgan, Petone (NZ)

(73) Assignees: Grante Seed Limited, Wellington (NZ); Roxdale Foods Limited, Auckland (NZ)

( * ) Notice: Subject to any disclaimer, the term of this patent is extended or adjusted under 35 U.S.C. 154(b) by 245 days.

(21) Appl. No.: 10/203,343

(22) PCT Filed: Feb. 7, 2001

(86) PCT No.: PCT/NZ01/00014

§ 371 (c)(1), (2), (4) Date: Jan. 13, 2003

(87) PCT Pub. No.: WO01/57092

PCT Pub. Date: Aug. 9, 2001

(65) Prior Publication Data

US 2003/0154974 A1 Aug. 21, 2003

(30) Foreign Application Priority Data

Feb. 7, 2000 (NZ) ..................................... 502731
Jul. 3, 2000 (NZ) ..................................... 505545

(51) Int. Cl.

*C08B 30/00* (2006.01)
*C07H 1/00* (2006.01)
*C07H 1/06* (2006.01)
*A61K 31/715* (2006.01)

(52) U.S. Cl. ................. 536/123.12; 536/124; 536/127; 536/128; 536/123.1; 536/23.6; 127/34; 424/195.1; 424/750; 424/94; 424/72; 426/28; 426/750; 426/573; 426/94; 426/18; 426/590; 510/392; 800/284

(58) Field of Classification Search ........... 536/123.12, 536/124, 127, 128, 123.1, 23.6; 127/34; 424/195.1, 750; 435/94, 72; 426/28, 750, 426/573, 94, 18, 590; 510/392; 800/284

See application file for complete search history.

(56) References Cited

U.S. PATENT DOCUMENTS

| | | | | |
|---|---|---|---|---|
| 4,804,545 | A * | 2/1989 | Goering et al. | 426/28 |
| 5,013,561 | A | 5/1991 | Goering et al. | 426/28 |
| 5,063,078 | A | 11/1991 | Foehse | 426/618 |
| 5,458,893 | A | 10/1995 | Smith | 426/18 |
| 5,725,901 | A | 3/1998 | Fox | 426/618 |
| 6,113,908 | A | 9/2000 | Paton et al. | 424/195.1 |
| 6,403,086 | B1 * | 6/2002 | Yegorova | 424/94.2 |
| 6,426,201 | B1 * | 7/2002 | Morgan | 435/99 |

FOREIGN PATENT DOCUMENTS

| | | | |
|---|---|---|---|
| WO | WO 92/10106 | * | 6/1992 |
| WO | WO 98/13056 | | 4/1998 |
| WO | WO 00/24270 | | 5/2000 |
| WO | WO 00/49052 | | 8/2000 |
| WO | WO 00/56268 | * | 9/2000 |

OTHER PUBLICATIONS

Luc Saulnier, et al., "Extraction and Partial Characterisation of β-glucan from the Endosperms of two Barley Cultivars", *Journal of Cereal Science*, vol. 19, pp. 171-178 (1994).

Peter J. Wood et al., "Large-Scale Preparation and Properties of Oat Fractions Enriched in (1-3)(1-4)-β-D-Glucan", *American Association of Cereal Chemists, Inc.*, vol. 66, No. 2, pp. 97-103 (1989).

Morgan et. al, "Glucagel, A Gelling β-Glucan from Barley", *Cereal Chemistry*, vol. 75, No. 6, pp. 879-881 (Nov.-Dec. 1998).

Beer, et al., "Extraction of Oat Gum from Oat Bran: Effect of Process on Yield, Molecular Weight Distribution, Viscosity and (1-3)(1-4)-β-D-Glucan Content of the Gum", Cereal Chemistry, 73(1):58-62, 1996.

* cited by examiner

*Primary Examiner*—Shaojia Anna Jiang
*Assistant Examiner*—Devesh Khare
(74) *Attorney, Agent, or Firm*—Fish & Richardson P.C.

(57) ABSTRACT

A process for obtaining β-glucan from cereal grain, such as barley and oats. A β-glucan product obtained by the process. Uses of the β-glucan product as a food ingredient and for treating various diseases or disorders. The process includes the steps of forming flour from the cereal grain, mixing the flour with water to form a slurry of a process for obtaining β-glucan from cereal grain including forming flour from the cereal grain, mixing the flour with water to form a slurry of an aqueous solution of β-glucan and a solid residue, separating the aqueous solution from the solid residue, and removing water from the aqueous solution by evaporation or ultrafiltration or combinations thereof to form a β-glucan containing gel or solid.

22 Claims, No Drawings

PROCESS FOR EXTRACTION OF β-GLUCAN FROM CEREALS AND PRODUCTS OBTAINED THEREFROM

FIELD OF INVENTION

This invention relates to a novel process for the extraction of β-glucan from cereals, such as barley and oats. The invention also relates to β-glucan products obtained from the process. The invention further relates to uses of those products as food ingredients and therapeutic agents.

BACKGROUND

The term "β-glucan" refers to those polysaccharides which comprise D-glucopyranosyl units which are linked together by (1→3) or (1→4) β-linkages. β-Glucans occur naturally in many cereal grains such as oats and barley. The molecular weight of β-glucan molecules occurring in cereals is typically 200 to 2000 kiloDaltons.

β-Glucan is desirable as a food additive, for example, to impart texture ("mouth feel") to foods or useful as edible films for food coatings. β-Glucan may also be used to add bulk to foods and has the advantage of having a neutral flavour.

β-Glucan is also desirable as a therapeutic agent. There is evidence that β-glucan can lower serum cholesterol levels, heal wounds, moderate glycaemic response, and alleviate constipation. β-Glucan can actively bind to specific cell receptors and therefore may be useful for the treatment of a wide variety of disorders or diseases.

The known methods for extracting β-glucan from cereal grains, such as oats and barley, involve several steps. Firstly, the cereal grain is milled to a flour prior to extracting β-glucan from the flour using warm or hot water or an aqueous alkali solution. The milling step facilitates release of the β-glucan from the cereal. The aqueous extract of β-glucan is then separated from the solid flour residue. Finally, the β-glucan is recovered from the extract.

The known methods of recovering the β-glucan from the aqueous extract include precipitation of the β-glucan using a water miscible solvent, such as alcohol, or by freezing and then thawing the extract to give a precipitate of β-glucan which can be recovered by filtration or centrifugation. The extraction of the β-glucan itself from the cereal is not generally a costly process. However, the recovery of the β-glucan from the extract is costly. This is due to the large amounts of water that must be removed to give solid β-glucan.

In addition, it is difficult to control the molecular weight of the β-glucan product obtained from known processes. High molecular weight β-glucan is preferable for certain uses. For example, high molecular weight β-glucan is preferable for moderating glycaemic response and for lowering serum cholesterol levels. On the other hand, low molecular weight β-glucan may be preferable as a food additive. For example, low molecular weight β-glucan can form a gel having beneficial textural properties for processed foods.

In order to obtain a high molecular weight β-glucan product, previous methods of β-glucan extraction from cereals have required that enzymes present in the cereal be deactivated prior to the extraction step. The enzymes are responsible for lowering β-glucan molecular weight and are deactivated either by treating the flour with boiling ethanol/water mixtures or by treating the flour with an aqueous acid solution.

SUMMARY OF INVENTION

It is an object of this invention to provide a process for extracting β-glucan from cereals and to provide a β-glucan product obtained from the process, or at least to provide a useful alternative process or product.

In one aspect of the invention there is provided a process for obtaining β-glucan from cereal grain including:

- forming flour from the cereal grain;
- mixing the flour with water at a temperature below approximately 65° C. to form a slurry of an aqueous solution of β-glucan and a solid residue;
- separating the aqueous solution from the solid residue;
- removing water from the aqueous solution by evaporation or ultrafiltration or combinations thereof to give a concentrated aqueous solution of β-glucan; and
- forming a β-glucan gel from the concentrated aqueous solution of β-glucan.

Although the cereal used may be any cereal containing β-glucan, the preferred cereal of the invention is barley or oats.

It is preferred that the gel is formed from the aqueous solution of β-glucan using any combination of the following steps: shearing, heating, cooling and freezing the solution. Shearing the solution may be by stirring the solution or by passing the solution down a pipe. The solution may also be heated and cooled to induce the formation of a gel. It is also preferred that the gel, once formed, is washed with water to remove starch or protein or starch or protein that may have been hydrolysed. The gel may also be frozen, for example by extrusion into a bath containing an aqueous solution of a salt where the temperature of the bath is below 0° C. The frozen gel is removed from the bath and then thawed to give a more compact gel which is more readily isolated by filtration. The gel may then be dried by, for example, spray drying or hot roller drying.

Preferably the step of milling the flour is carried out under dry conditions to enable the removal of starch from the cereal. Starch granules can be removed from the milled flour by sieving or by air classification. Alternatively, the cereal may be milled in the presence of either cold water or a mixture of ethanol and water to facilitate the removal of starch by standard methods.

The invention therefore also provides a starch rich fraction obtained from the process of this invention and useful as an ingredient in processed foods, for malting, or as a feed for animals.

It is preferred in the extraction step that the flour is mixed with water at a temperature greater than 45° C. but less than approximately 60° C.

Preferably the aqueous solution of β-glucan is separated from the solid residue by centrifugation or by filtration.

The invention therefore also provides a solid residue obtained from this process and useful as an ingredient in processed foods, for malting, or as a feed for animals.

The β-glucan is recovered from the aqueous solution by firstly concentrating the aqueous solution of β-glucan. Concentration of the aqueous solution may be by evaporation, for example thin-film evaporation, or ultrafiltration, to form a concentrated aqueous solution. A β-glucan gel can be formed from this solution. The gel may be washed with water to remove impurities and then dried, for example by spray drying or hot roller drying, to obtain a β-glucan solid.

Prior to concentrating the aqueous solution of β-glucan, it is preferable to remove starch and/or protein impurities. Protein may be removed by heating the aqueous solution to above about 70° C. causing the protein to precipitate which can then be removed by filtration or by decanting or by centrifugation.

Alternatively, protein may be removed by adding a protease to the aqueous solution followed by ultrafiltration of the degraded protein. Another method of removing protein is to add a flocculant such as a carrageenan, for example κ-carrageenan. Starch may also be removed by adding a starch degrading enzyme, such as an α-amylase, to the aqueous solution followed by ultrafiltration to remove the degraded starch.

It is preferable during β-glucan extraction to add an enzyme to reduce the average molecular weight of the β-glucan. The enzyme is preferably a cellulase (for example, E.C. 3.2.1.4).

It is also preferable during β-glucan extraction to degrade any arabinoxylans present by adding an arabinoxylan degrading enzyme, for example, a xylanase.

The invention also provides a β-glucan product produced by a process of this invention.

The invention further provides a composition containing β-glucan obtained by a process of this invention.

The invention also provides a method for lowering serum cholesterol levels in an animal including administering to the animal a β-glucan product obtained by a process of this invention.

The invention also provides a method for healing a wound in an animal including administering to the animal a β-glucan product obtained by the process of the invention.

The invention also provides a method for moderating glycaemic response in an animal including administering to the animal a β-glucan product obtained by the process of this invention.

The invention also provides a method for alleviating constipation in an animal including administering to the animal a β-glucan product obtained by the process of this invention.

The invention also provides a method for stimulating the immune system in an animal including administering to the animal a β-glucan product obtained by the process of this invention.

The invention also provides a food ingredient containing a β-glucan product obtained by the process of this invention.

The invention further provides an edible film as a food coating prepared using β-glucan obtained by the process of this invention.

DETAILED DESCRIPTION

β-Glucan occurs naturally in a wide variety of cereals. The process of this invention is not limited to any particular cereal. However, preferred cereals are barley and oats.

The process of this invention can be varied to give different β-glucan products. The physical properties of a β-glucan product are dependent principally on the average molecular weight of the β-glucan molecules and the conformation of the β-glucan molecules. High molecular weight β-glucan is β-glucan having an average molecular weight greater than $5\times10^5$ Daltons. Low molecular weight β-glucan is β-glucan having an average molecular weight in the range of $5\times10^3$ to $2\times10^5$ Daltons.

β-Glucan products can form a gel in water. The ease with which a β-glucan product forms a gel depends on the average molecular weight of the β-glucan and also depends on the manner in which a solution of β-glucan extracted from cereal grain is processed.

High molecular weight β-glucan is desirable for certain therapeutic uses because of its high viscosity in aqueous solution. The moderation of glycaemic response and the lowering of serum cholesterol levels can be effected using β-glucan of high molecular weight. However, enzymes known to degrade β-glucan from high molecular weight β-glucan to low molecular weight β-glucan are known to be present in cereal grains. Therefore, known methods of obtaining a β-glucan from cereals have required an enzyme deactivation step, such as treatment with boiling ethanol/water mixtures or by treatment with an aqueous acid solution.

However, it is known that in some cereals, particularly barley, the β-glucan degrading enzymes are present in the husk and outer layers of the grain. Thus, removal of the husk and outer layers of the grain by pearling leaves a cereal grain which has little or no β-glucan degrading enzyme present. In addition, the outer layers of the grain (the aleurone and sub-aleurone layers) are depleted in β-glucan. The pearled grain is therefore enriched in β-glucan relative to unpearled grain.

During aqueous extraction of β-glucan from unpearled grain, colour, flavour, and enzymes from the husks of the grain can appear in the extract. Following further processing, this can result in a β-glucan product having an unacceptable colour or flavour, or being degraded by the enzymes. Pearling of the grain removes the husks and outer layers and therefore minimises any undesirable colour or flavour of the β-glucan product.

During mixing of the flour with water to extract the β-glucan, the water may be at any temperature in the range of 25 to 65° C. However, the temperature of the water is preferred to be approximately 45 to 60° C. Preferably the pH of the mixture is in the range 2 to 10.

Starch is the major constituent of the grain and occurs as small granules within the grain. β-Glucan occurs within the cell walls of the grain which surround the starch granule. The complete or partial removal of starch from flour obtained from the grain would therefore result in a fraction enriched in β-glucan. An enriched β-glucan fraction has the following benefits. Firstly, there would be less solid material to remove after the extraction was complete. The extract would contain more β-glucan for a given volume of water used. Therefore, less concentration of the extract would be required. Finally, less starch would be solubilised during the extraction since there is less starch in the flour from which the β-glucan is extracted.

Various methods are known for complete or partial removal of starch from cereal grain. These include dry milling and wet milling. Wet milling with water has a disadvantage since about 30–50% of the cell wall β-glucan is soluble in water at a temperature of 25° C. However, only 10–20% of the cell wall β-glucan is soluble in ice-cold water. Similarly, little of the cell wall β-glucan is soluble in ethanol or ethanol/water mixtures or aqueous solutions of certain salts. Therefore, for wet milling, it is preferable to use cold water or ethanol/water mixtures or aqueous solutions of certain salts.

Dry milling may be used for removing starch. A large proportion of the starch can be removed from dry flour by sieving or air classification. The cell wall material containing the β-glucan mostly occurs as particles which are larger than the starch granules after milling. Consequently, the starch granules will pass through the sieve while cell wall material will be retained. Air classification will separate out the dense starch granules from the cell wall material. However, it is to be understood that these methods of separation are not 100% efficient and that the starch fraction will contain some cell wall material and the cell wall material will contain some starch.

The β-glucan from the enriched β-glucan material can now be extracted using hot water. Since there are little or no β-glucan degrading enzymes left in the grain, it can be useful to add an enzyme, preferably a cellulase, to the extraction solution to partially degrade the β-glucan in a controlled fashion. This also helps release the β-glucan from the enriched material. It can also be advantageous to add an arabinoxylan degrading enzyme, preferably a xylanase, since these degrade unwanted arabinoxylans in the extract, decreasing the extract viscosity, increasing the yield of extract after separation from the solids, and also helping in the release of the β-glucan from the enriched flour.

After extraction the solids are preferably removed by centrifugation. The extract can be concentrated at this stage by evaporation of all or some of the water. Such techniques for this are well known and include thin-film evaporation to obtain a concentrated β-glucan solution, and spray drying or hot roller drying to obtain a β-glucan containing solid.

The final product from this process contains protein and starch. In some cases this less pure form of β-glucan may be the preferred product. However, it may be desirable to remove the starch and/or protein prior to water evaporation to obtain a product of higher purity. Starch can be degraded using a starch degrading enzyme, preferably α-amylase, and protein can be degraded by a protein degrading enzyme, that is, a protease. The degraded starch and protein can then be removed from the extract and the extract concentrated by ultrafiltration. It is also possible to precipitate the protein by heating the extract above about 70° C. The precipitated protein can then be separated from the solution of the extract. Heating the extract above 70° C. has the advantage of also destroying any remaining enzyme activity and sterilising the extract.

Heating the extract above about 70° C. appears to inhibit gel formation. Heated extracts appear not to form a precipitate when frozen and thawed nor do they gel readily, that is, within a few hours. However, gelation can be induced by the following methods, either alone or in combination with other methods. Resting the solution for a period of time, shearing the solution for a period of time, cooling the solution for a period of time, heating the solution for a period of time, and freezing the solution for a period of time. Generally it is easier to induce gelation with more concentrated solutions, especially those containing low molecular weight β-glucan.

Inducing gelation at this stage of the process has several advantages over the technique of freezing and then thawing the solution. The expense of freezing in some cases can be avoided. Where freezing is still required the solutions are more concentrated, thus decreasing the cost of freezing.

Following gelation it may be preferable to freeze the gel, for example by extrusion into a bath containing a salt, where the bath is at a temperature of less than 0° C. The gel is then recovered and thawed to give a compact gel which can be more easily filtered.

Finally after gelation has been induced it can be advantageous to wash out the hydrolysed or unhydrolysed starch and protein contaminants from the β-glucan gel before the gel is dried to obtain a β-glucan enriched gel.

The starch rich fraction obtained from sieving or air-classification could be a valuable product useful in baked and processed foods. Similarly, after the extraction of the β-glucan from the grain the wet solids remaining contain significant amounts of β-glucan. These wet solids could be dried and used in processed foods. The β-glucan in the dried solids could have useful texturising properties in a variety of processed foods. It is also possible that the starch fraction or the wet solids could be used for malting or sold as feed for animals.

The invention is described with reference to the following examples but is not to be construed as limited thereto.

In the examples all β-glucan contents were determined using the Megazyme Mixed-Linkage Assay Procedure and the McCleary method or a modification of the McCleary method. The starch and malto-oligosaccharide contents were determined using the Megazyme Total Starch Assay Procedure or a modification of this procedure (Megazyme International Ireland Ltd, Bray Business Park, Bray, Co. Wicklow, Ireland)

EXAMPLE 1

Barley grain (50 g) was pearled from 40 to 60% and then finely milled in a Kenwood mixer with milling attachment. The milled grain was sieved through sieves of sizes 150, 90 and 63 μm. The coarse fraction left on the sieve was further ground with a mortar pestle and sieved again. Yields, percentage and absolute β-glucan contents for each fraction are shown in Table 1.

TABLE 1

| Fraction | Sieve size/μm | Yield/g | β-glucan content % | β-glucan content/g |
| --- | --- | --- | --- | --- |
| Coarse | >150 | 12.9 | 7.61 | 0.981 |
| Medium | 150 → 90 | 6.06 | 12.53 | 0.760 |
| Fine | 90 → 63 | 2.32 | 11.55 | 0.268 |
| Very fine | <63 | 25.72 | 0.85 | 0.218 |

The very fine fraction was the largest fraction sieved but contained only small amounts of β-glucan. The medium and fine fractions both contained about 12% β-glucan. Of the sieved flour fraction 83% of the β-glucan occurred in the fraction that sieved between 150 and 60 μm.

EXAMPLE 2

The release of β-glucan from the medium sieved fraction obtained in Example 1 was determined in the presence of various enzymes: a cellulase (*Trichoderma reesei* species from Sigma, 6.3 U/ml), xylanase (Shearzyme™ from Novo Nordisk, activity unknown) and protease (Alaclase™ from Novo Nordisk, 2.4 AU/g). The medium sieved fraction (1 g, see Example 1) was added to various combinations of enzymes (see Table 2) in water (7 ml) and the mixture was heated for 1.5 h at 50° C. to extract β-glucan. The β-glucan extract was separated from the solids by centrifuging at 3500 rpm for 10 min and then frozen. After thawing, the yield of precipitated (ppt) β-glucan was determined. The results are shown in Table 2.

TABLE 2

| *T. reesei* | Shearzyme | Alaclase | Yield of extract /ml | Yield of ppt β-glucan/g |
|---|---|---|---|---|
| 10 ul | 10 ul | 10 ul | 5.67 | 0.061 |
| 5 ul | 10 ul | 0 | 5.44 | 0.061 |
| 0 | 10 ul | 10 ul | 5.73 | 0.051 |
| 5 ul | 0 | 0 | 5 | 0.03 |

All the enzymes appeared to be effective in increasing the yield of ppt β-glucan but the Shearzyme™/cellulase combination appeared to be most effective. The yield of extract after centrifuging was improved by adding Shearzyme™.

EXAMPLE 3

A flour enriched in β-glucan was prepared by sieving a barley pollard flour. The β-glucan was extracted from the flour by heating a mixture of the flour (2 g) with water (10 ml) to which had been added cellulase (10 μL, *Trichoderma reesei* species from Sigma, 6.3 U/ml) at 50° C. for 30 min. The extract (6.1 ml) was separated from the solids by centrifuging at 3000 rpm for 15 min. The extract was then heated on a boiling water bath for 5 min to, precipitate protein, which was removed by centrifugation. The extract was evaporated to dryness by rotary evaporation, which produced a glassy film containing about 53% β-glucan.

EXAMPLE 4

A barley pollard flour 10 g was mixed with water (50 ml) and heated at 50° C. for 1 h. The extract was separated from the solids by centrifuging at 3000 rpm for 10 min. This yielded 30 ml of extract. The extract was then heated to 95° C. for 10 min and the protein that precipitated was removed on a centrifuge. The extract was concentrated on rotary evaporator to about 25% of its original volume. The extract was then stirred rapidly for 2 min to induce shearing and then rested for 5 min. This procedure was repeated 6 times before the extract was frozen for 12 h. No precipitate formed on thawing. Over a period of days the solution slowly thickened. After 2 days the solution was frozen and thawed again. This produced a precipitate, which was filtered, washed with water and dried. The yield was 0.16 g.

EXAMPLE 5

A pollard flour (30 g) was mixed with water (150 ml) containing Shearzyme™ (10 μL, Novo Nordisk, activity unknown,) and cellulase (50 μL, *Trichoderma reesei* species from Sigma, 6.3 U/ml). The mixture was heated at 50° C. for 1.5 h. After 30 min the mixture was found to be reasonably free flowing. A β-glucan extract was recovered from the mixture by removing the solids on a centrifuge. The yield of extract was 118 ml.

The extract was treated in a number of ways.

a) 25 ml of the extract was filtered through glass fibre then treated with amylase (200 μL, Bacillus species Sigma, 3480U/ml) for 1 h 30 min at 30° C. to hydrolyse the starch in the extract. The extract was then heated at 90° C. for 15 min and centrifuged (3,000 rpm 10 min) to remove protein and destroy amylase activity. The liquid recovered was 23 ml. The extract was dialysed overnight to remove hydrolysed starch. The extract was then evaporated to an oil in a rotary evaporator and oven dried at 80° C. The β-glucan content of the oven dried material was about 57%.

b) 25 ml of the extract was heated at 90° C. for 15 min then centrifuged to remove protein. The liquid recovered was 23 ml. The extract was rotary evaporated to about half its original volume and then dried as a thin film in an oven at 80° C. The β-glucan content of the film was about 30%. Approximately 0.2 g of the film was dissolved in 2 ml of water at 90° C. to form a transparent solution. The solution was cooled in ice and stirred to induce shearing and then rested. This was repeated several times. After leaving overnight a gel had formed. The gel was frozen. The thawed gel was washed with water and filtered and dried. The gel filtered very readily on a #3 sintered glass filter. This yielded 0.066 g of dried gel. The β-glucan content of the dried gel was 87%.

c) 25 ml of the extract was filtered through glass fibre and then treated with amylase (200 μL, Bacillus species Sigma, 3480U/ml) for 30 min at 30° C. to hydrolyse the starch in the extract. The extract was heated at 90° C. for 15 min and centrifuged (3,000 rpm 10 min) to remove protein and destroy amylase activity. The extract (0.4 ml) was placed in an ultrafiltration centrifugal filter unit (Millipore Ultrafree-MC). The filter unit was centrifuged (13,000 rpm for 40 minutes) and about 0.07 ml of liquid was recovered which was oven dried to a thin transparent film.

EXAMPLE 6

Barley pollard flour (30 g) was mixed with water (150 ml) containing Shearzyme™ (10 μL, Novo Nordisk, activity unknown) and cellulase (50 μL, *Trichoderma reesei* species from Sigma, 6.3 U/ml). The mixture was heated on a water bath at 50° C. for 1.5 h. After 30 min the mixture was found to be reasonably free flowing. The solids were removed from the mixture by centrifuging and the extract that remained was heated at 90° C. for 15 min. The protein that precipitated was removed on a centrifuge. The yield of extract was 118 ml. The extract was concentrated to 17 ml by rotary evaporation. A viscous solution remained which was heated to 90° C. and cooled and then heated to 70° C. and cooled. This caused the solution to set rapidly to a soft gel, which was dispersed in water to remove soluble impurities, and then filtered and dried. The yield of dried gel was 0.71 g. The β-glucan content of the dried gel was 80%. The washings from the gel were rotary evaporated to an oil and then oven dried. This yielded 0.9 g of a glassy material. The β-glucan content of the glassy material was 4%. Therefore it appears that about 94% of the β-glucan was in the dried gel and only 6% in the gel washings obtained by filtering the gel.

EXAMPLE 7

The following examples illustrates a novel method for removing starch which does not result in much solubilisation of β-glucan.

Removal of starch from the cell-wall material was accomplished by homogenising in a Kenwood mixer, barley flour (4 g) with water that was saturated with a salt, in this case sodium sulphate. The solution was filtered through a 55 μm nylon mesh. The slurry filtered well, indicating little or no solubilisation of the β-glucan. Remaining on the filter was the enriched cell-wall fraction (1.75 g) which contained 10.4% β-glucan.

EXAMPLE 8

A gel is formed by concentrating a β-glucan extract. Barley flour (25 g) was mixed with water (175 ml) and a xylanase (6.2 μL, Shearzyme from Novo Nordisk, activity unknown) and cellulase (125 μL, Penisillum funicolsum 0.1 mg /ml) was added. The extraction solution was heated at 50° C. for 1 h. The extract was separated from the solids by centrifuging at 3500 rpm for 10 min. The extract was then heated at 90° C. for 10 min to precipitate protein, which was removed by filtering through a glass fibre filter. The extract was concentrated to 1/10 its original volume and left overnight in the fridge to gel. After heating the gel to 65° C. and then cooling the gel, the gel was firmer.

EXAMPLE 9

More β-glucan can be extracted from finely ground flour then coarsely ground flour. For each of the medium and the coarse flour fractions prepared in example 1, the flour (0.2 g) was mixed with water (2 ml) to which a xylanase (0.1 μL, Shearzyme from Novo Nordisk, activity unknown) and cellulase (5 μL, Penicillium funicolusum from Sigma, 10 μg/ml) had been added. The extraction was continued at 50° C. for 1 h. The extract was separated from the solids by centrifuging at 3500 rpm for 10 min. The β-glucan content of the extract was then measured. For the medium flour fraction about 70% of the β-glucan in the flour was extracted, whereas for the coarse material only about 50% of the β-glucan was extracted.

EXAMPLE 10

Barley flour (5 g ) was mixed with water (35 ml) to which a xylanase (Shearzyme from Novo Nordisk, activity unknown) and a cellulase (Celluclast from Novo Nordisk, 1500 NCU/g) had been added according to the quantities given in Table 3. The extraction solution was heated at 50° C. for 2 h. The extract was separated from the solids by centrifuging at 3500 rpm for 10 min. The extract was then heated at 90° C. for 10 min to precipitate protein, which was removed by centrifuging. After a freeze/thaw of the extract the precipitate of β-glucan solids in the thawed liquid was filtered, and washed with water then ethanol. The solids were dried and the viscosity of a 1% solution measured. Mw, the weight average molecular weight was estimated from the viscosity using the method of Böhm, N. and Kulicke, W-M. Carbohydr. Res. 315 (1999) 293–301, and are shown in Table 3.

TABLE 3

| Shearzyme added/μL | Celluclast added/μL | Relative viscosity | Mw |
|---|---|---|---|
| 2 | 0.2 | 49 | 19000 |
| 2 | 0.02 | 123 | 75000 |
| 2 | 0 | 300 | 194000 |

The molecular weight thus can be altered by changing the quantities of β-glucan degrading enzyme added to the reaction mixture.

EXAMPLE 11

It is advantageous to use cold-water to wash out the starch and cause minimum solubilisation of the β-glucan. Barley flour (0.2 g) containing 8.5% β-glucan was mixed with water (2 ml) at 4.5° C. for 2 h. The extract was separated from the solids by centrifuging at 3500 rpm for 10 min. From the β-glucan content of the extract it was calculated that only about 5% of the β-glucan in the flour was solubilised.

EXAMPLE 12

For maximum protein precipitation the pH of the extract should be near the isoelectric point of the protein. Barley flour (10 g) was mixed with water (70 ml) and the extract mixture was heated at 50° C. for 1 h. The extract was separated from the solids by centrifuging at 3500 rpm for 10 min. A portion (5 ml) of the extract was taken and the pH adjusted to 7.0 with NaOH solution (0.1 M). On heating to 95° C. no protein precipitation was observed.

EXAMPLE 13

To decrease the amounts of starch and maltodextrins in the extracts it is advantageous to deactivate partially or completely the native amylases in the flour, which improves the purity and gel properties of the β-glucan. Acid treatment and heating was found to be effective in deactivating the amylases.

A solution of the amylase was prepared by mixing barley flour (20 g) with water (200 ml) and immediately centrifuging the mixture. The supernatant was then filtered with Glass fibre (Watman GF/A) to remove fines. The supernatant was then treated by adjusting the pH and heating. Amylase activity of the supernatant was measured by mixing an equal amount of the treated supernatant with a potato starch solution (1.5%) and recording the decrease in viscosity. Results are shown in Table 4.

TABLE 4

| Code | Treatment of supernatant | Viscosity after 1 min | Viscosity after 5 min | Viscosity after 10 min | Viscosity after 20 min |
|---|---|---|---|---|---|
| A | None | 70 | 63 | 59 | 55 |
| B | Heated at 95° C. for 15 min | 87 | 90 | 89 | 88 |
| C | PH adjusted to 3.8 then heated at 50 ° C. for 25 min, pH | 90 | 90 | 89 | 86 |

TABLE 4-continued

| Code | Treatment of supernatant | Viscosity after 1 min | Viscosity after 5 min | Viscosity after 10 min | Viscosity after 20 min |
|---|---|---|---|---|---|
| | then adjusted to 5.4. | | | | |

For a) the untreated supernatant showed significant enzyme activity. With b) heating at 95° C. destroyed amylase activity. For c) adjusting to pH = 3.8 and then heating at 50° C. destroyed most of the enzyme activity. There was only a small decrease in the viscosity of the potato starch solution after the pH of the supernatant was adjusted back to 5.4 (pH = 5.4 is near the optimum pH for amylase activity).

EXAMPLE 14

Protein precipitation by addition of a precipitating agent such as carrageenan can be useful for removing additional amounts of protein. This improves the purity and gelling properties of the β-glucan. For optimum protein precipitation the pH of the solution should be below the isoelectric point of the protein.

A flour from a pearled barley (5 g) was mixed with water (35 ml) to which had been added a xylanase (2 μL, Shearzyme from Novo Nordisk) and a cellulase (0.05 μL. Celluclast from Novo Nordisk, 1500 NCU/g). Dilute HCl (200 μL, 0.1 M) and carrageenan (150 μL, 1%, Viscarin BF 136C from FMC) was added. A brown precipitate forms which was removed by centrifuging.

EXAMPLE 15

Sieved barley fractions were prepared enriched in β-glucan. Barley (5.1% β-glucan content) was pearled to a weight loses of 30%. The grain was milled on the finest setting of a Kenwood mixer fitted with a grain mill attachment. Of the flour formed, 5 g was hand sifted through two successive sieves containing a 150 and 63 micron mesh. The coarse material retained as the over on the 150 micron sieve was ground in a mortar and pestle until most past through the 150 micron sieve. Three fractions were obtained as shown in Table 5.

TABLE 5

| Code | Sieve size/micron | Yield | β-glucan content/% | β-glucan % of total |
|---|---|---|---|---|
| a | >150 | 0.20 | 9.4 | 9 |
| b | 150 → 63 | 0.83 | 16.8 | 65 |
| c | <63 | 3.33 | 1.7 | 26 |

From table 5 it can be seen that 65% of the β-glucan was concentrated in the fraction over the 63 micron sieve and that the β-glucan content of this fraction was about 16%.

EXAMPLE 16

The stability of a gel that had been frozen was tested by repeated washings with water. The gel (4.9 g) was filtered on a 55 μm mesh to remove excess water and the filtrate retained. The gel was then washed with water (10 ml) and the second filtrate retained. The β-glucan content of the filtrates and gel were measured. Results shown in the table indicate little solubilisation of β-glucan in the gel during washing.

TABLE 6

| Sample | β-glucan content/% | % of total β-glucan |
|---|---|---|
| First filtrate | 0.15 | 2% |
| Second filtrate | 0.014 | 0.7% |
| Gel | 11.7 | 97% |

EXAMPLE 17

Amylase deactivation lessens the amount of maltose and starch solubilised during extraction. Water (10 ml) was adjusted to pH=2.4 with HCl (~0.65 ml, 1.0 M) and added to flour (10 g) milled from a pearled barley. For this mixture the pH was found to be 2.8. The mixture was heated at 50° C. for 20 min on a water bath to deactivate the amylase. The pH of the mixture was then adjusted to 5.5 with NaOH (2 ml, 1.0 M). A xylanase (4 μL, Shearzyme Novo Nordisk) and a cellulase (0.1 μL Celluclast from Novo Nordisk) was added to the extraction mixture and the extraction continued for 1 h. The mixture was then centrifuged at (3000 rpm, 5 min) and the supernatant retained. The solution was then acidified with HCl (1.6 ml, 0.1 M) and κ-carrageenan (1.2 ml, 1%) was added. The precipitate that was formed was removed by centrifuging to give a bright solution. The solution was lyophilised to a whitish solid. The above experiment was repeated, but no enzyme deactivation step was included.

The starch/malto-oligosaccharide content of the solids with and without amylase deactivation was 9% and 26%, respectively.

EXAMPLE 18

An extract was formed from flour obtained from pearled barley according to Example 17 (with amylase deactivation). The solution obtained after protein precipitation was rotary evaporated to an oil and left at 4° C. for 2 days. During this time the oil set to a gel, which was washed several times with water. The gel was pressed between paper towels to remove excess water. Solids content of the gel was 17% of which 75.6% was β-glucan. Some 50% of the β-glucan in the flour was recovered in the gel.

EXAMPLE 19

Barley (1000 kg) was pearled to produce pearl barley (700 kg). The pearl barley was milled through two roller mills and a hammer mill and then screened to produce two flour fractions. The first fraction (420 kg) contained approximately 80% of the β-glucan. The second fraction (280 kg) contained approximately 20% of the β-glucan. The second fraction was discarded. The first fraction was divided into seven batches (each 69 kg).

Each batch was mixed into warm water (1200 L) to give a mixture at a temperature of 50° C. Cellulase (0.5 ml, Celluclast from Novo Nordisk, 1500 NCU/g) and Xylanase (60 ml, Shearzyme from Novo Nordisk, activity unknown) enzymes were added to the mixture which was stirred and held for 60 minutes. The mixture was then passed through a solid bowl decanter and a centrifugal clarifier to remove all insoluble material. The insoluble material was discarded.

The resulting liquid extract (900 L) was adjusted to a pH of 4.5. Amyloglucosidase enzyme (150 ml, AMG 300 L from Novo Nordisk, 300 ACU/g) was then added to hydrolyse any soluble starch. After the extract was shown to be starch negative, it was heated to 95° C. for 15 minutes and then centrifuged to remove the insoluble protein.

The extract from all seven batches was combined and filtered through a diatomaceous earth filter. The filtered extract was then concentrated in a triple effect falling film evaporator, followed by a single effect scraped surface evaporator, to approximately 12% total solids. The concentrate was then cooled at less than 0° C. for 24 hours to develop a suitable gel structure. The gel was then washed in cold water to remove the remaining soluble sugars and other soluble material.

The gel was recovered from the mixture using a centrifugal clarifier and then dried in a spray drier to approximately 5% moisture to give β-glucan powder (14 kg). The powder was a fine, free flowing pale cream β-glucan powder. The β-glucan content was approximately 85% on a dry solids basis and had a molecular weight of approximately 50,000d.

EXAMPLE 20

A liquid extract was prepared according to Example 19 above but was subjected to ultrafiltration following filtration through the diatomaceous earth filter, rather than concentration in a triple effect falling film evaporator.

The extract (500 L) was collected after diatomaceous earth filtration and was purified and concentrated using an ultrafiltration membrane. The extract was circulated through a spiral type ultrafiltration membrane. The membrane had an area of approximately 6.4 sq. metres and a nominal molecular cut-off of 10kd. Circulation was continued until the volume of the circulate was reduced to 100 L. Water (100 L) was added and the circulation was continued until the volume was reduced again to 100 L. At the end of the process, 80% of the liquid had been removed as permeate and the β-glucan purity had increased from 35% to 60% of total solids.

Although the invention has been described by way of example, it should be appreciated that variations and modifications may be made thereto without departing from the invention.

Furthermore, where known equivalents exist to specific features, such equivalents are incorporated as if specifically set forth herein.

INDUSTRIAL APPLICABILITY

The β-glucan products of this invention are useful as food additives and as therapeutic agents. They provide desirable texture to foods, can be used as edible films for food coatings, and can be used as bulking agents in foods. The products of the invention are also useful as therapeutic agents including agents for lowering serum cholesterol levels, healing wounds, moderating glycaemic response, alleviating constipation, and stimulating the immune system.

The invention claimed is:

1. A process for obtaining a β-glucan gel from cereal grain including:
- forming flour from the cereal grain;
- mixing the flour with water at a temperature in the range of 25–65° C. to form a slurry of an aqueous solution of β-glucan and a solid residue;
- separating the aqueous solution from the solid residue;
- removing water from the aqueous solution by evaporating or ultrafiltration or combinations thereof to give a concentrated aqueous solution of β-glucan; and
- forming a β-glucan gel from the concentrated aqueous solution of β-glucan.

2. A process as claimed in claim 1 wherein the flour is formed by pearling the cereal grain to remove the husk and outer layer of the cereal grain and then milling the pearled cereal grain.

3. A process as claimed in claim 1 wherein the pH of the water is adjusted either before or after mixing with the flour.

4. A process as claimed in claim 3 wherein the pH is adjusted to less than 4.0 and the slurry is then heated to greater than 40° for at least 10 minutes to deactivate amylases in the flour.

5. A process as claimed in claim 4 wherein the pH is readjusted to greater than 4.0 after heating.

6. A process as claimed in claim 1 wherein the flour is mixed with water at a temperature of 45° C. to 60° C.

7. A process as claimed in claim 1 wherein the flour is mixed with water at a temperature of 50° C. for 15 to 60 minutes.

8. A process as claimed in claim 1 further including adding an enzyme to the slurry to degrade any arabinoxylans which may be present in the slurry.

9. A process as claimed in claim 1 where an enzyme is added to the slurry to assist the release of β-glucan from the flour.

10. A process as claimed in claim 1 wherein the aqueous solution is separated from the solid residue by centrifugation followed by decantation or by filtration.

11. A process as claimed in claim 1 wherein an enzyme is added to the aqueous solution to degrade starch.

12. A process as claimed in claim 1 wherein an enzyme is added to the slurry or to the aqueous solution to reduce the average molecular weight of the β-glucan.

13. A process as claimed in claim 1 wherein a protease is added to the aqueous solution to degrade proteins.

14. A process as claimed in claim 1 further including heating the aqueous solution to precipitate protein.

15. A process as claimed in claim 1 further including adding a flocculant to the aqueous solution to precipitate protein.

16. A process as claimed in claim 1 further including drying the gel.

17. A process as claimed in claim 1 wherein the β-glucan gel formation is conducted by shearing the concentrated aqueous solution, heating the concentrated aqueous solution, or cooling the concentrated aqueous solution.

18. A process as claimed in claim 1 further including one or more of:
- freezing the gel and then thawing to increase the density or compactness of the gel after the second forming step;
- washing the gel with water to remove impurities, such as starch or protein or fragments thereof after the second forming step; or
- removing impurities from the aqueous solution by ultrafiltration and diafil tration after the separating step and before the second forming step.

19. A process as claimed in claim 1 wherein the flour is formed by milling the cereal grain under dry conditions and then removing starch granules by sieving or by air classification.

20. A process as claimed in claim 1 wherein the flour is formed by milling the cereal grain in the presence of either cold water or a mixture of ethanol and water, or an aqueous salt solution, and then removing starch.

21. A process as claimed in claim 1 wherein the cereal is barley or oats.

22. A process as claimed in claim 1, wherein the β-glucan gel formation is conducted by heating and then cooling the concentrated aqueous solution.

* * * * *